(12) United States Patent
Dickinson et al.

(10) Patent No.: US 9,101,405 B2
(45) Date of Patent: Aug. 11, 2015

(54) VERTEBRAL IMPLANT AND CONNECTOR

(75) Inventors: Charles Anthony Dickinson, Bartlett, TN (US); Alan Rezach, Atoka, TN (US); Andrea Watt, Cordova, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 26 days.

(21) Appl. No.: 13/371,130

(22) Filed: Feb. 10, 2012

(65) Prior Publication Data
US 2013/0211457 A1 Aug. 15, 2013

(51) Int. Cl.
*A61B 17/70* (2006.01)

(52) U.S. Cl.
CPC ......... *A61B 17/7041* (2013.01); *A61B 17/7055* (2013.01)

(58) Field of Classification Search
CPC .................. A61B 17/701–17/7037; A61B 17/7049–17/7052
USPC ........... 606/246–279, 301–324, 330; 403/362
See application file for complete search history.

(56) References Cited

U.S. PATENT DOCUMENTS

| 5,209,752 | A | * | 5/1993 | Ashman et al. ............... 606/278 |
| 5,261,909 | A | * | 11/1993 | Sutterlin et al. .............. 606/264 |
| 5,344,422 | A | * | 9/1994 | Frigg ........................... 606/278 |
| 5,609,592 | A | * | 3/1997 | Brumfield et al. ........... 606/250 |
| 5,667,506 | A | * | 9/1997 | Sutterlin ....................... 606/252 |
| 5,741,255 | A | * | 4/1998 | Krag et al. .................... 606/264 |
| 5,876,403 | A | * | 3/1999 | Shitoto ......................... 606/308 |
| 6,001,098 | A | * | 12/1999 | Metz-Stavenhagen et al. ............................. 606/264 |
| 6,231,575 | B1 | * | 5/2001 | Krag ............................. 606/264 |
| 6,551,318 | B1 | * | 4/2003 | Stahurski ...................... 606/252 |
| 7,585,312 | B2 | * | 9/2009 | Rawlins et al. ............... 606/246 |
| 7,927,353 | B2 | * | 4/2011 | Taylor et al. .................. 606/246 |
| 8,262,702 | B2 | * | 9/2012 | Giger et al. ................... 606/252 |
| 8,317,834 | B2 | * | 11/2012 | Rezach et al. ................. 606/264 |
| 8,414,623 | B2 | | 4/2013 | Baker et al. .................. 606/278 |
| 8,668,721 | B2 | * | 3/2014 | Miller ........................... 606/264 |
| 8,715,323 | B2 | * | 5/2014 | Ballard et al. ................ 606/278 |
| 2004/0054371 | A1 | * | 3/2004 | Dierks et al. .................... 606/73 |
| 2006/0129150 | A1 | * | 6/2006 | Suzuki et al. ................... 606/61 |
| 2007/0238335 | A1 | * | 10/2007 | Veldman et al. .............. 439/157 |
| 2008/0021455 | A1 | * | 1/2008 | Chao et al. ..................... 606/61 |
| 2008/0086126 | A1 | * | 4/2008 | Miller ............................ 606/61 |
| 2009/0036929 | A1 | * | 2/2009 | Reglos et al. ................. 606/278 |
| 2009/0287253 | A1 | * | 11/2009 | Felix et al. .................... 606/278 |
| 2010/0049253 | A1 | * | 2/2010 | Miller ........................... 606/264 |
| 2010/0057140 | A1 | * | 3/2010 | Zucherman et al. .......... 606/308 |
| 2011/0098748 | A1 | * | 4/2011 | Jangra .......................... 606/278 |
| 2012/0179205 | A1 | * | 7/2012 | Miller ........................... 606/264 |
| 2013/0150895 | A1 | * | 6/2013 | McLean et al. ............... 606/278 |
| 2013/0184760 | A1 | * | 7/2013 | Ballard et al. ................ 606/278 |
| 2014/0052189 | A1 | * | 2/2014 | Hammer ....................... 606/278 |

* cited by examiner

*Primary Examiner* — Eduardo C Robert
*Assistant Examiner* — Michelle C Eckman (57) ABSTRACT

An implant system comprises a fastener including a proximal portion including an inner surface that defines a first cavity that defines a first axis and a distal portion configured for penetrating tissue and defining a longitudinal axis disposed transverse to the first axis. A connector extends between a first end and a second end configured for disposal in the first cavity. A receiver is attachable to the first end and includes an implant cavity defining a second axis. The implant cavity is rotatable about a third axis disposed transverse to the second axis such that an implant disposed in the implant cavity and lateral to the first end is rotatable in a first plane relative to the first end in a configuration for selective fixation with the first end. Methods of use are disclosed.

20 Claims, 7 Drawing Sheets

FIG. 7 ns through the first axis, a connector extending between a first end and a second end configured for disposal in the first cavity, and a receiver attachable to the first end of the connector and including an implant cavity defining a second axis, the implant cavity being rotatable about a third axis disposed transverse to the second axis; attaching the distal portion of the fastener with iliac bone; disposing an implant in the implant cavity such that the implant is lateral to the first end of the connector; selectively rotating the implant in a first plane relative to the first end of the connector; and locking the receiver with the connector in a selected angular orientation of the implant relative to the connector.

VERTEBRAL IMPLANT AND CONNECTOR

TECHNICAL FIELD

The present disclosure generally relates to medical devices for the treatment of musculoskeletal disorders, and more particularly to a spinal implant system and method that employs a connector and provides stabilization of vertebrae, which may include the sacroiliac region.

BACKGROUND

Spinal disorders such as degenerative disc disease, disc herniation, osteoporosis, spondylolisthesis, stenosis, scoliosis and other curvature abnormalities, kyphosis, tumor, and fracture may result from factors including trauma, disease and degenerative conditions caused by injury and aging. Spinal disorders typically result in symptoms including pain, nerve damage, and partial or complete loss of mobility. For example, after a disc collapse, severe pain and discomfort can occur due to the pressure exerted on nerves and the spinal column. In another example, disorders of the sacroiliac joint can cause low back and radiating buttock and leg pain in patients.

Non-surgical treatments, such as medication, injection, mobilization, rehabilitation and exercise can be effective, however, may fail to relieve the symptoms associated with these disorders. Surgical treatment of these spinal disorders includes fusion, fixation, discectomy, laminectomy and implantable prosthetics. During surgical treatment, one or more rods may be attached via fasteners to the exterior of two or more vertebral members. Fasteners may also be attached to iliac bone. The present disclosure describes an improvement over these prior art technologies.

SUMMARY

Accordingly, a surgical system and method is provided. In one particular embodiment, in accordance with the principles of the present disclosure, an implant system comprises a fastener including a proximal portion and a distal portion. The proximal portion includes an inner surface that defines a first cavity that defines a first axis. The distal portion is configured for penetrating tissue and defines a longitudinal axis disposed transverse to the first axis. A connector extends between a first end and a second end configured for disposal in the first cavity. A receiver is attachable to the first end of the connector and includes an implant cavity defining a second axis. The implant cavity is rotatable about a third axis disposed transverse to the second axis such that an implant disposed in the implant cavity and lateral to the first end of the connector is rotatable in a first plane relative to the first end of the connector in a configuration for selective fixation with the first end of the connector.

In one embodiment, the implant system comprises an iliac bone screw including a posterior head and an anterior threaded shaft configured to penetrate bone. The posterior head includes an inner surface that defines a first cavity that defines a first axis. The inner surface includes axial splines oriented along the first axis and circumferentially disposed about the inner surface. The distal portion defines a longitudinal axis disposed transverse to the first axis. A connector extends between a first end and a second end. The first end includes a first disk having a first face including a threaded shaft extending in a posterior orientation therefrom and defines a first splined surface. The second end includes an outer surface comprising axial splines circumferentially disposed thereabout. The axial splines of the posterior head are engageable with the axial splines of the second end in a configuration for selective angular fixation of the iliac bone screw with the connector. A receiver includes a second disk having a second splined surface that mates with the first splined surface and defines an opening configured for disposal of the shaft. The receiver further includes a nut engageable with the threaded shaft to retain the receiver with the connector. The receiver further includes a laterally extending arcuate arm that defines an implant cavity defining a second axis. The implant cavity is rotatable about a third axis disposed transverse to the second axis such that a vertebral rod disposed in the implant cavity and lateral to the first end of the connector is selectively rotatable in a coronal plane of a body relative to the first end of the connector in a configuration for selective angular fixation with the first end of the connector.

In one embodiment, a method for treating a disorder is provided. The method comprises the steps of providing an implant system comprising: a fastener including a proximal portion and a distal portion, the proximal portion including an inner surface that defines a first cavity that defines a first axis, the distal portion defining a longitudinal axis disposed transverse to the first axis, a connector extending between a first end and a second end configured for disposal in the first cavity, and a receiver attachable to the first end of the connector and including an implant cavity defining a second axis, the implant cavity being rotatable about a third axis disposed transverse to the second axis; attaching the distal portion of the fastener with iliac bone; disposing an implant in the implant cavity such that the implant is lateral to the first end of the connector; selectively rotating the implant in a first plane relative to the first end of the connector; and locking the receiver with the connector in a selected angular orientation of the implant relative to the connector.

BRIEF DESCRIPTION OF THE DRAWINGS

The present disclosure will become more readily apparent from the specific description accompanied by the following drawings, in which.

Like reference numerals indicate similar parts throughout the figures.

DETAILED DESCRIPTION

The exemplary embodiments of the implant system and methods disclosed are discussed in terms of medical devices for the treatment of musculoskeletal disorders and more particularly, in terms of an implant system and method for treating a disorder. In one embodiment, the implant system includes a vertebral implant, such as, for example, a spinal rod and an iliac connector disposed with an iliac screw. It is envisioned that the implant system and methods disclosed may provide stability to a portion of the anatomy of a patient, such as, for example, vertebrae, a sacroiliac (SI) joint, iliac bone and maintain structural integrity while reducing stress on the SI joint and/or portions of the anatomy adjacent the SI joint.

In one embodiment, the implant system includes an iliac connector having a connecting element disposed lateral to a vertebral implant. This configuration disposes a substantial portion of the connector material lateral to a spinal rod to minimize a profile of the implant system posterior to the spinal rod. In one embodiment, the implant system includes a connector that can lock at different angles in a coronal plane of a body of a patient. This configuration facilitates connection of a spinal rod to an iliac screw and avoids rod bending due to misalignment of the component parts.

It is envisioned that the present disclosure may be employed to treat spinal disorders such as, for example, degenerative disc disease, disc herniation, osteoporosis, spondylolisthesis, stenosis, scoliosis and other curvature abnormalities, kyphosis, tumor and fractures. It is contemplated that the present disclosure may be employed with other osteal and bone related applications, including those associated with diagnostics and therapeutics. It is further contemplated that the disclosed system and methods may be alternatively employed in a surgical treatment with a patient in a prone or supine position, and/or employ various surgical approaches to the spine, including anterior, posterior, posterior mid-line, lateral, postero-lateral, and/or antero-lateral approaches, and in other body regions. The present disclosure may also be alternatively employed with procedures for treating the lumbar, cervical, thoracic and pelvic regions of a spinal column. The system and methods of the present disclosure may also be used on animals, bone models and other non-living substrates, such as, for example, in training, testing and demonstration.

The present disclosure may be understood more readily by reference to the following detailed description of the disclosure taken in connection with the accompanying drawing figures, which form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value. Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure. For example, the references "upper" and "lower" are relative and used only in the context to the other, and are not necessarily "superior" and "inferior".

Further, as used in the specification and including the appended claims, "treating" or "treatment" of a disease or condition refers to performing a procedure that may include administering one or more drugs to a patient (human, normal or otherwise or other mammal), in an effort to alleviate signs or symptoms of the disease or condition. Alleviation can occur prior to signs or symptoms of the disease or condition appearing, as well as after their appearance. Thus, treating or treatment includes preventing or prevention of disease or undesirable condition (e.g., preventing the disease from occurring in a patient, who may be predisposed to the disease but has not yet been diagnosed as having it). In addition, treating or treatment does not require complete alleviation of signs or symptoms, does not require a cure, and specifically includes procedures that have only a marginal effect on the patient. Treatment can include inhibiting the disease, e.g., arresting its development, or relieving the disease, e.g., causing regression of the disease. For example, treatment can include reducing acute or chronic inflammation; alleviating pain and mitigating and inducing re-growth of new ligament, bone and other tissues; as an adjunct in surgery; and/or any repair procedure. Also, as used in the specification and including the appended claims, the term "tissue" includes soft tissue, ligaments, tendons, cartilage and/or bone unless specifically referred to otherwise.

Figure 1:
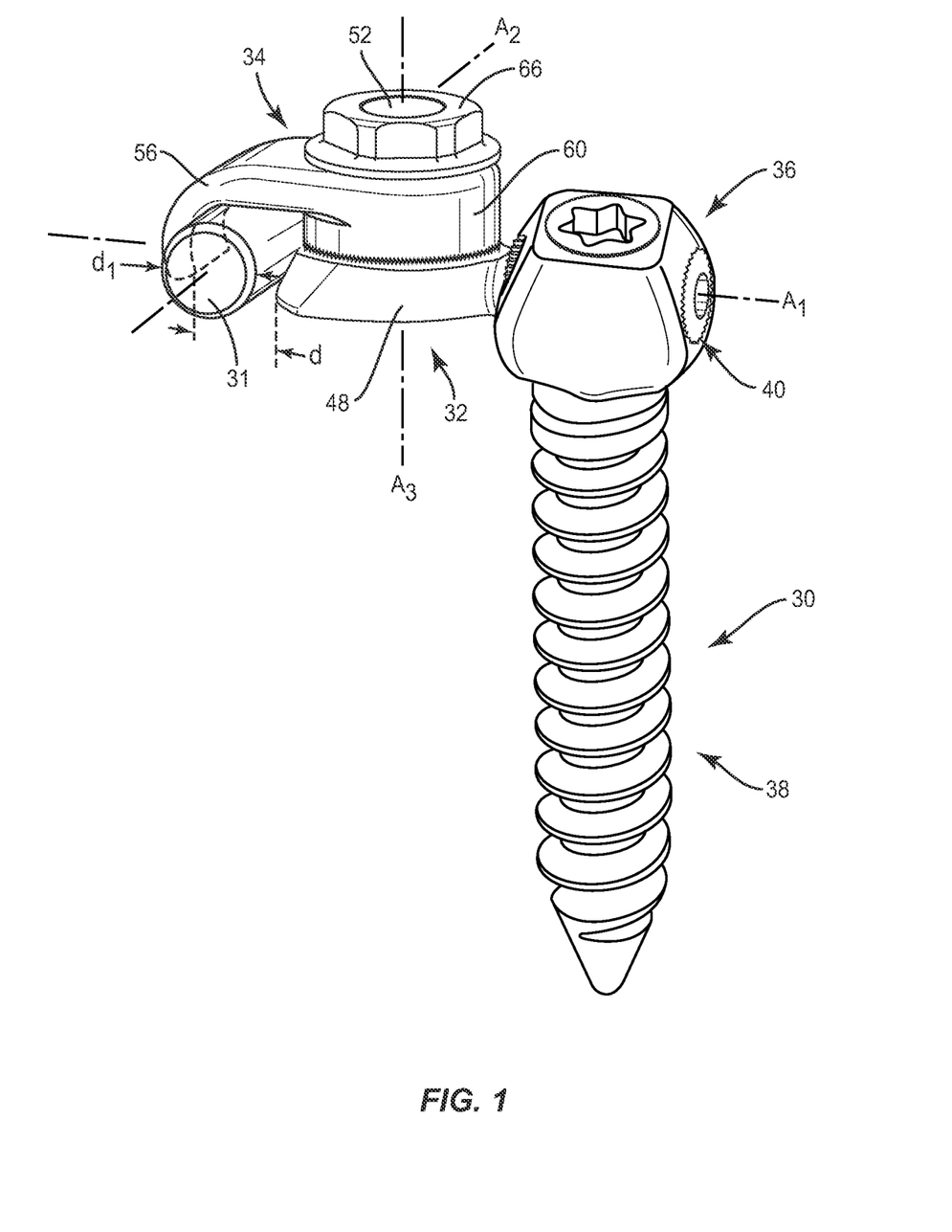
FIG. 1 is a perspective view of one particular embodiment of an implant system in accordance with the principles of the present disclosure.
Figure 2:
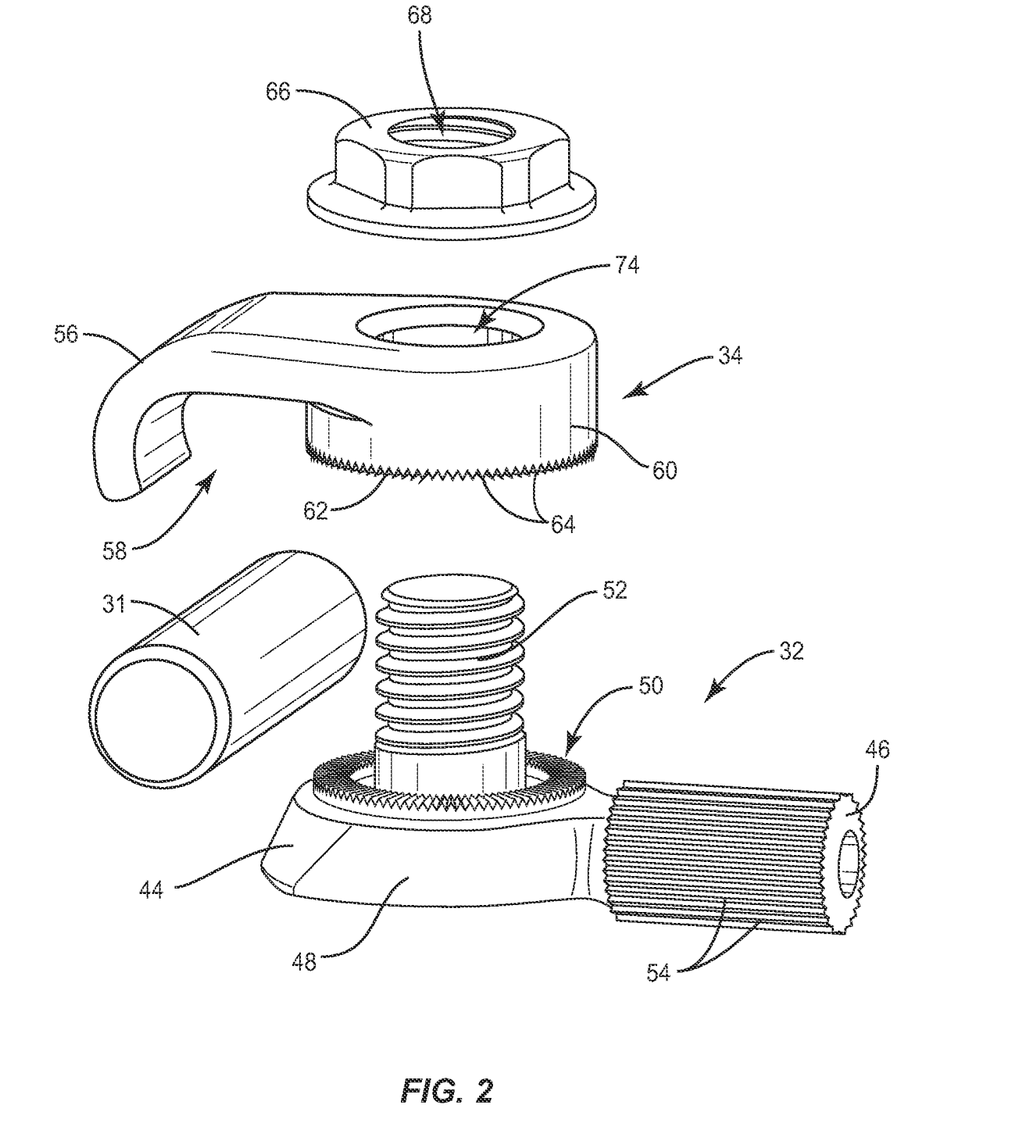
FIG. 2 is a perspective view of components of the implant system shown in FIG. 1 with parts separated.

The following discussion includes a description of a surgical system including an implant system, related components and exemplary methods of employing the implant system in accordance with the principles of the present disclosure. Alternate embodiments are also disclosed. Reference will now be made in detail to the exemplary embodiments of the present disclosure, which are illustrated in the accompanying figures. Turning now to FIGS. 1 and 2, there is illustrated components of a surgical system including an implant system in accordance with the principles of the present disclosure.

The components of the implant system can be fabricated from biologically acceptable materials suitable for medical applications, including metals, synthetic polymers, ceramics and bone material and/or their composites, depending on the particular application and/or preference of a medical practitioner. For example, the components of the implant system, individually or collectively, can be fabricated from materials such as stainless steel alloys, commercially pure titanium, titanium alloys, Grade titanium, super-elastic titanium alloys, cobalt-chrome alloys, stainless steel alloys, superelastic metallic alloys (e.g., Nitinol, super elasto-plastic metals, such as GUM METAL® manufactured by Toyota Material Incorporated of Japan), ceramics and composites thereof such as calcium phosphate (e.g., SKELITE™ manufactured by Biologix Inc.), thermoplastics such as polyaryletherketone (PAEK) including polyetheretherketone (PEEK), polyetherketoneketone (PEKK) and polyetherketone (PEK), carbon-PEEK composites, PEEK-BaSO4 polymeric rubbers, polyethylene terephthalate (PET), fabric, silicone, polyurethane, silicone-polyurethane copolymers, polymeric rubbers, polyolefin rubbers, hydrogels, semi-rigid and rigid materials, elastomers, rubbers, thermoplastic elastomers, thermoset elastomers, elastomeric composites, rigid polymers including polyphenylene, polyamide, polyimide, polyetherimide, polyethylene, epoxy, bone material including autograft, allograft, xenograft or transgenic cortical and/or corticocancellous bone, and tissue growth or differentiation factors, partially resorbable materials, such as, for example, composites of metals and calcium-based ceramics, composites of PEEK and calcium based ceramics, composites of PEEK with resorbable polymers, totally resorbable materials, such as, for example, calcium based ceramics such as calcium phosphate, tri-calcium phosphate (TCP), hydroxyapatite (HA)-TCP, calcium sulfate, or other resorbable polymers such as polyaetide, polyglycolide, polytyrosine carbonate, polycaroplaetohe and their combinations. Various components of the implant system may have material composites, including the above materials, to achieve various desired characteristics such as strength, rigidity, elasticity, compliance, biomechanical performance, durability and radiolucency or imaging preference. The components of the implant system, individually or collectively, may also be fabricated from a heterogeneous material such as a combination of two or more of the above-described materials. The components of the implant system may be monolithically formed, integrally connected or include fastening elements and/or instruments, as described herein.

The implant system is configured for attachment to vertebrae and/or iliac bone (as shown, for example, in FIG. 3) during surgical treatment of a spinal disorder, examples of which being discussed herein. The implant system includes a fastener, such as, for example, an iliac bone screw 30, a connector 32 and a receiver 34. It is envisioned that the implant system may include one or a plurality of fasteners, connectors and/or receivers.

Bone screw 30 includes a proximal portion, such as, for example, a posterior head 36 and a distal portion, such as, for example, an anterior threaded shaft 38 configured to penetrate bone. Head 36 includes an inner surface that defines a first cavity 40 that defines a first axis $A_1$. First cavity 40 is configured to receive and movably support at least a portion of connector 32 such that connector 32 can translate axially within first cavity 40 along first axis $A_1$ through a first plane, such as, for example, a coronal plane of a body. It is contemplated that connector 32 may be disposed with bone screw 30 for relative movement thereto in orientations relative to first axis $A_1$, such as, for example, transverse, perpendicular and/or other angular orientations such as acute or obtuse, co-axial and/or may be offset or staggered. It is further contemplated that connector 32 may move relative to bone screw 30 in alternate planes relative to a body, such as, for example, transverse and/or sagittal planes of a body.

First cavity 40 has a tubular configuration so as to form a passageway through bone screw 30 and for receiving a portion of connector 32 that extends through head 36 of bone screw 30. It is envisioned that all or only a portion of first cavity 40 may be variously configured and dimensioned, such as, for example, oval, oblong, square, rectangular, polygonal, irregular, uniform, non-uniform, offset, staggered, tapered, consistent or variable, depending on the requirements of a particular application. In one embodiment, first cavity 40 may extend through only a portion of head 36 and not completely through.

First cavity 40 of head 36 includes axial splines 42 (not shown) circumferentially disposed about the inner surface of head 36 oriented along first axis $A_1$. First cavity 40 provides at least a portion of a mounting and alignment configuration for mating bone screw 30 with connector 32 and receiver 34 during a surgical treatment. Axial splines 42 in first cavity 40 include a plurality of individual spline members that extend in parallel relation about first cavity 40. Axial splines 42 in first cavity 40 mate with splines on connector 32 to align and mount bone screw 30 with connector 32 when bone screw 30 is connected with connector 32.

Anterior threaded shaft 38 defines a longitudinal axis L disposed transverse to first axis $A_1$. It is contemplated that anterior threaded shaft 38 may be disposed in other orientations relative to first axis $A_1$, such as, for example, perpendicular and/or other angular orientations such as acute or obtuse, co-axial and/or may be offset or staggered. Shaft 38 has a cylindrical cross section configuration and includes an outer surface having an external thread form. It is contemplated that the thread form may include a single thread turn or a plurality of discrete threads. It is further contemplated that other engaging structures may be located on shaft 38, such as, for example, a nail configuration, barbs, expanding elements, raised elements and/or spikes to facilitate engagement of shaft 38 with tissue, such as, for example, vertebrae and/or iliac bone.

It is envisioned that all or only a portion of shaft 38 may have alternate cross section configurations, such as, for example, oval, oblong, triangular, square, polygonal, irregular, uniform, non-uniform, offset, staggered, undulating, arcuate, variable and/or tapered. It is contemplated that the outer surface of shaft 38 may include one or a plurality of openings. It is further contemplated that all or only a portion of the outer surface of shaft 38 may have alternate surface configurations to enhance fixation with tissue such as, for example, rough, arcuate, undulating, mesh, porous, semi-porous, dimpled and/or textured according to the requirements of a particular application. It is envisioned that all or only a portion of shaft 38 may be cannulated.

In one embodiment, head 36 of bone screw 30 has a reduced thickness at a distal end of head 36 and an increased thickness at a proximal end of head 36 to enhance the low profile configuration of bone screw 30 with a body. As such, head 36 is tapered such that at least a portion of head 36 may seat more closely with the anatomy of a patient, thereby reducing the profile of bone screw 30. In one embodiment, at least a portion of an outer surface of head 36 is threaded for penetration with a body surface such that bone screw 30 has a low profile when fixed with a body of a patient. It is envisioned that the threads on the outer surface of head 36 may be continuous with the threads on shaft 38.

Connector 32 extends between a first end 44 and a second end 46. First end 44 includes a first disk 48 having an upper surface defining a first face defining a first splined surface 50. First splined surface 50 of first disk 48 is configured to mate with splines on a surface of receiver 34 to releasably fix receiver 34 with connector 32 in a selected rotatable position in a first plane, such as, for example, a coronal plane of the body relative to shaft 38 of bone screw 30. First disk 48 is disposed in a co-axial orientation with second end 46 of connector 32 and/or an implant engaged with receiver 34. First disk 48 is substantially circular. It is envisioned that all or only a portion of first disk 48 may have alternate cross section configurations, such as, for example, oval, oblong, triangular, square, polygonal, irregular, uniform, non-uniform, offset, staggered, undulating, arcuate, variable and/or tapered.

First disk 48 includes a first locking part, such as, for example, a threaded shaft 52 extending in a posterior orientation from the first face of first disk 48 configured to engage a second locking part, such as, for example, a nut to retain receiver 34 with connector 32. It is contemplated that threaded shaft 52 may be disposed in other orientations relative to the first face of first disk 48, such as, for example, perpendicular and/or other angular orientations such as acute or obtuse, co-axial and/or may be offset or staggered. It is envisioned that receiver 34 may be coupled with connector 32 in alternate fixation configurations, such as, for example, friction fit, pressure fit, locking protrusion/recess, locking keyway and/or adhesive. It is further envisioned that receiver 34 may be disposed with connector 32 for relative movement thereto, such as, for example, transverse, perpendicular and/or other angular orientations such as acute or obtuse, co-axial and/or may be offset or staggered. It is contemplated that receiver 34 may move relative to connector 32 in alternate planes relative to a body, such as, for example, transverse and/or sagittal planes of a body. It is further contemplated that all or only a portion of first splined surface 50 of first disk 48 may have alternate surface configurations to enhance fixation with receiver 34, such as, for example, rough, arcuate, undulating, mesh, porous, semi-porous, dimpled and/or textured according to the requirements of a particular application.

Second end 46 of connector 32 includes a cylindrical outer surface comprising axial splines 54 circumferentially disposed about the outer surface of second end 46. Axial splines 54 are engageable with axial splines 42 disposed about the inner surface of first cavity 40 in head 36 of bone screw 30 for selective angular fixation of the bone screw 30 with connector 32. Axial splines 54 include a plurality of individual spline members that extend in parallel relation about the outer surface of second end 46. The configuration of axial splines 54 provides at least a portion of a mounting and alignment configuration for aligning and mounting bone screw 30 with connector 32 and receiver 34 during a surgical treatment. It is envisioned that the outer surface of second end 46 may have alternate cross section configurations, such as, for example, oval, oblong, triangular, rectangular, square, polygonal, irregular, uniform, non-uniform, variable and/or tapered. It is further envisioned that all or only a portion of the outer surface of second end 46 may have alternate surface configurations, such as, for example, rough, threaded for connection with other instruments, arcuate, undulating, porous, semi-porous, dimpled, polished and/or textured according to the requirements of a particular application.

Second end 46 of connector 32 is configured for disposal within first cavity 40 of bone screw 30 along axis $A_1$ in the coronal plane of the body for selective fixation in a position along axis $A_1$. Second end 46 of connector 32 is moveable along axis $A_1$ relative to shaft 38 of bone screw 30. It is envisioned that second end 46 may be inserted into first cavity 40. Second end 46 is moved within first cavity 40 in the coronal plane along axis $A_1$, in a first axial direction or a second axial direction oriented in an opposing direction to the first axial direction, by sliding second end 46 relative to first cavity 40. First cavity 40 is engageable with second end 46 to align the component parts in relative rotatable alignment in angular increments about their relative circumferential surfaces. The angular increments correspond to a spline teeth angle of splines 42, 54. It is contemplated that the spline teeth angle may be in a range of approximately 5 to 20 degrees.

Receiver 34 is attachable to first end 44 of connector 32 and is selectively rotatable in the transverse plane of the body and selectively fixable in a position within the transverse plane. Receiver 34 includes a body portion having a laterally extending arcuate arm 56 defining a posterior opening, such as, for example, an implant cavity 58 defining a second axis $A_2$. It is envisioned that arcuate arm 56 may also define an anterior opening configured to receive an implant. Arcuate arm 56 has a substantially semi-circular cross section such that implant cavity 58 has an open portion at a distal end thereof. As shown in FIG. 2, first disk 48 is tapered between lower and upper surfaces thereof such that a distance d between the lower surface of first disk 48 and a posterior portion of arcuate arm 56 is less than a diameter d1 of rod 31 so as to prevent rod 31 from being advanced proximally through the open portion of implant cavity 58 and into implant cavity 58. It is contemplated that at least a portion of an exterior surface of rod 31 rests against at least a portion of first end 44 of connector 32 and at least a portion of an interior surface of arcuate arm 56 when rod 31 is inserted into implant cavity 58, as shown in FIG. 2. It is envisioned that implant cavity 58 may be cylindrical such that an interior surface of implant cavity 58 surrounds the entire exterior surface of an implant inserted into implant cavity 58. It is further contemplated that the outer surface of second end 46 may have alternate cross section configurations, such as, for example, oval, oblong, triangular, rectangular, square, polygonal, irregular, uniform, non-uniform, variable and/or tapered.

Implant cavity 58 is configured to receive and movably support at least a portion of an implant, such as, for example, a vertebral rod 31, such that rod 31 can translate axially within implant cavity 58 along second axis $A_2$. Implant cavity 58 is rotatable about a third axis $A_3$ disposed transverse to second axis $A_2$ such that an implant disposed in implant cavity 58 and lateral to first end 44 of connector 32 is rotatable in a first plane, such as, for example, a coronal plane of the body, relative to first end 44 of connector 32 in a configuration for selective fixation with first end 44 of connector 32. It is contemplated that at least a portion of the implant may be disposed within implant cavity 58 for relative movement in orientations relative to second axis $A_2$, such as, for example, transverse, perpendicular and/or other angular orientations such as acute or obtuse, co-axial and/or may be offset or staggered. It is further contemplated that at least a portion of the implant may be disposed within implant cavity 58 in alternate planes relative to a body, such as, for example, transverse and/or sagittal planes of a body. In one embodiment, implant cavity 58 may be disposed at an angle of about 30 to about 150 degrees relative to first cavity 40 of bone screw 30 and second axis $A_2$ may be disposed at an angle of about to about 150 degrees relative to first axis $A_1$.

Receiver 34 includes a second disk 60 having a first face defining a second splined surface 62 defined by axial splines 64 that mate with the splines on first splined surface 50 of first disk 48 to releasably fix receiver 34 with connector 32 in a selected rotatable position in a plane, such as, for example, a coronal plane of the body relative to shaft 38 of bone screw 30. It is contemplated that all or only a portion of second splined surface 62 may have alternate surface configurations to enhance fixation with connector 32, such as, for example, rough, arcuate, undulating, mesh, porous, semi-porous, dimpled and/or textured according to the requirements of a particular application. Splines 64 and the splines on first splined surface 50 of first disk 48 are configured to mesh such that receiver 34 (including implant cavity 58) and second disk 60 can rotate and lock at different angles relative to connector 32 in the transverse plane such that implant cavity 58 may rotate about third axis $A_3$ such that a vertebral rod disposed in implant cavity 58 and posterior to first end 44 of connector 32 is selectively rotatable in a coronal plane of a body relative to first end 44 of connector 32 in a configuration for selective angular fixation with first end 44 of connector 32. It is envisioned that implant cavity 58 (or an implant received within implant cavity 58) may be rotated through an angle of 0 to 360 degrees relative to connector 32. Second disk 60 is locked in position relative to first disk 48 by forcing disks 48, 60 into engagement. In one embodiment, disks 48, 60 are resiliently biased towards one another for fixed engagement.

Second disk 60 includes an opening 74 extending through second disk 60 having a diameter which is greater than that of threaded shaft 52 of connector 32 such that threaded shaft 52 may be disposed within opening 74 to retain connector 32 with receiver 34. Threaded shaft 52 has a height which is greater than the width of receiver 34 such that at least a portion of threaded shaft 52 will extend proximal to receiver 34 when connector 32 is retained with receiver 34 by inserting threaded shaft 52 into opening 74. A nut 68 defines an opening 68 having threads configured to mate with the threads of threaded shaft 52 to retain nut 68 on threaded shaft 52.

Figure 3:
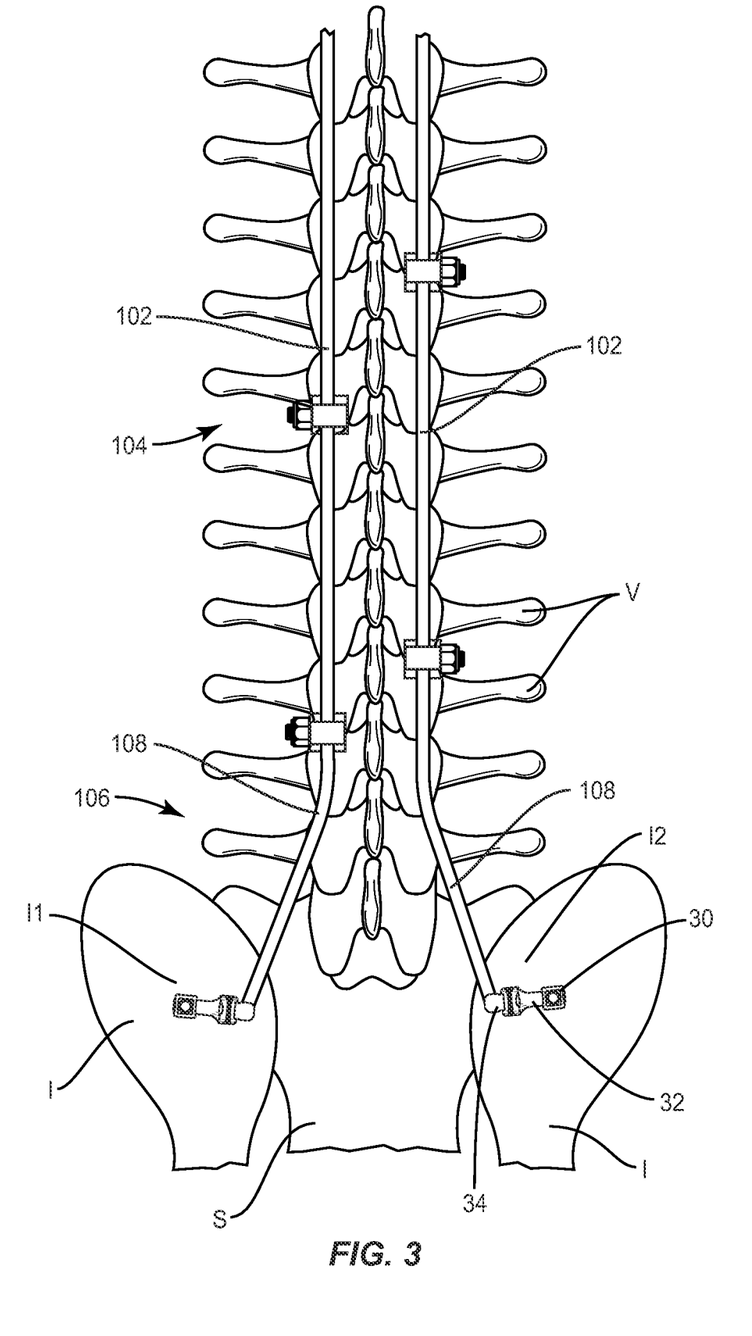
FIG. 3 is a plan view of one embodiment of an implant system in accordance with the principles of the present disclosure attached with vertebrae and an iliac bone of a patient.

In assembly, operation and use, the implant system including bone screw 30, connector 32, receiver 34 and nut 68 is employed with a surgical procedure for treatment of a spinal disorder affecting a section of a spine and/or ilium bones of a pelvis of a patient, as discussed herein. The implant system may also be employed with other surgical procedures. The implant system is employed with a surgical procedure for treatment of a condition or injury of an affected section of the spine including vertebrae V, which may include sacrum S, and/or ilium I, as shown in FIG. 3. It is contemplated that the implant system including bone screw 30, connector 32, receiver 34 and nut 68 is attached to vertebrae V and/or ilium I for a surgical arthrodesis procedure, such as fusion, and/or dynamic stabilization application of the affected section of the spine to facilitate healing and therapeutic treatment.

In use, to treat the affected section of the spine and/or ilium bones of a pelvis, a medical practitioner obtains access to a surgical site including vertebra V and/or ilium I in any appropriate manner, such as through incision and retraction of tissues. It is envisioned that the implant system including bone screw 30, connector 32, receiver 34 and nut 68 may be used in any existing surgical method or technique including open surgery, mini-open surgery, minimally invasive surgery and percutaneous surgical implantation, whereby the vertebrae V and/or ilium I is accessed through a micro-incision, or sleeve that provides a protected passageway to the area. Once access to the surgical site is obtained, the particular surgical procedure is performed for treating the bone disorder. The implant system including bone screw 30, connector 32, receiver 34 and nut 68 is then employed to augment the surgical treatment. The implant system including bone screw 30, connector 32, receiver 34 and nut 68 can be delivered or implanted as a pre-assembled device or can be assembled in situ. The implant system may be completely or partially revised, removed or replaced.

In one embodiment, the implant system includes one or a plurality of vertebral rods 102, bone screws 30, connectors 32, receivers 34 and nuts 68 for attaching rods 102 to vertebrae V, as shown in FIG. 3. The implant system of the present disclosure extends from a first portion 104 to a second portion 106 disposed adjacent a sacroiliac region (SIR) of the patient. Second portion 106 includes two axially aligned and spaced apart rods 102. Rods 102 each have a rigid, arcuate portion 108 extending across a sacrum S and ilium I of the SIR. A first bone fastener 30 is configured for fixation with an ilium surface I1 and a second bone fastener 30 is configured for fixation with an ilium surface I2. Pilot holes are made in ilium surfaces I1, I2 for receiving first and second bone screws 30. Each threaded shaft 38 of first and second bone screws 30 are inserted or otherwise connected to ilium surfaces I1, I2, according to the particular requirements of the surgical treatment. Connector 32 is attached with bone screw 30, and receiver 34 is attached with connector 32, as described above.

According to the orientation and position of each arcuate portion 108, connector 32 is aligned in relative rotatable alignment with first cavity 40 of bone screw 30. Second end 46 of connector 32 is configured for disposal within first cavity 40 of bone screw 30 along axis $A_1$ in the coronal plane of the body for selective fixation in a position along axis $A_1$. Second end 46 is moved within first cavity 40 in the coronal plane along axis $A_1$, in a first axial direction or a second axial direction oriented in an opposing direction to the first axial direction according to the orientation and position of each arcuate portion 108, by sliding second end 46 relative to first cavity 40.

Each receiver 34 may be rotated relative to each connector 32 such that arcuate portion 108 of each rod 102 may be moved within implant cavity 58 of receiver 34 by sliding arcuate portion 108 within implant cavity 58 such that each rod 102 is lateral to first end 44 of connector 32. At least a portion of rod 102 contacts at least a portion of first end 44 of connector 32 when rod 102 is inserted into implant cavity 58 so as to maintain rod 102 within implant cavity 58. Implant cavity 58 is selectively rotated relative to third axis $A_3$ in a first plane, such as, for example, the coronal plane of the patient corresponding to the orientation and position of each arcuate portion 108. This configuration allows orientation of implant cavity 58 to receive each arcuate portion 108 for disposal of each arcuate portion 108 therein. Nut 66 is then inserted onto threaded shaft 52 of first disk 48 by positioning opening 68 of nut 66 over threaded shaft 52 and rotating nut 66 such that the threads of nut 68 mate with the threads of threaded shaft 52 to lock receiver 34 with connector 32 in the selected rotation orientation. As nut 66 is threaded onto threaded shaft 52, the splined surfaces of disks 48, 60 are brought into fixed engagement to lock receiver 34 and connector 32 in the selected rotation orientation. It is contemplated that the implant system configuration of bone screw 30, connector 32, receiver 34 and nut 68 allows the implant system to be disposed close to a body surface, so as to be low profile, while retaining adjustability and maintaining strength of fixation and/or attachment with the body surface.

Figure 4:
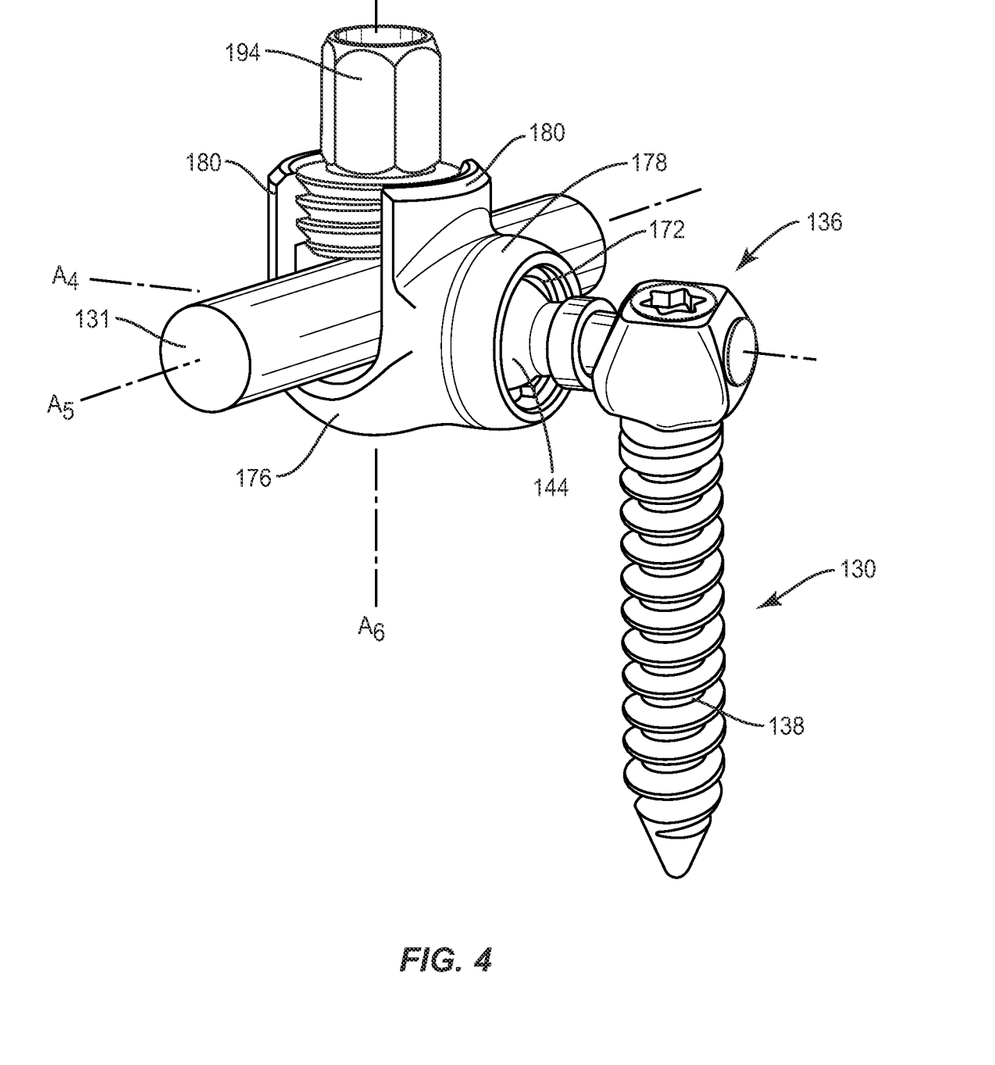
FIG. 4 is a perspective view of one embodiment of components of the implant system shown in FIG. 1.
Figure 5:
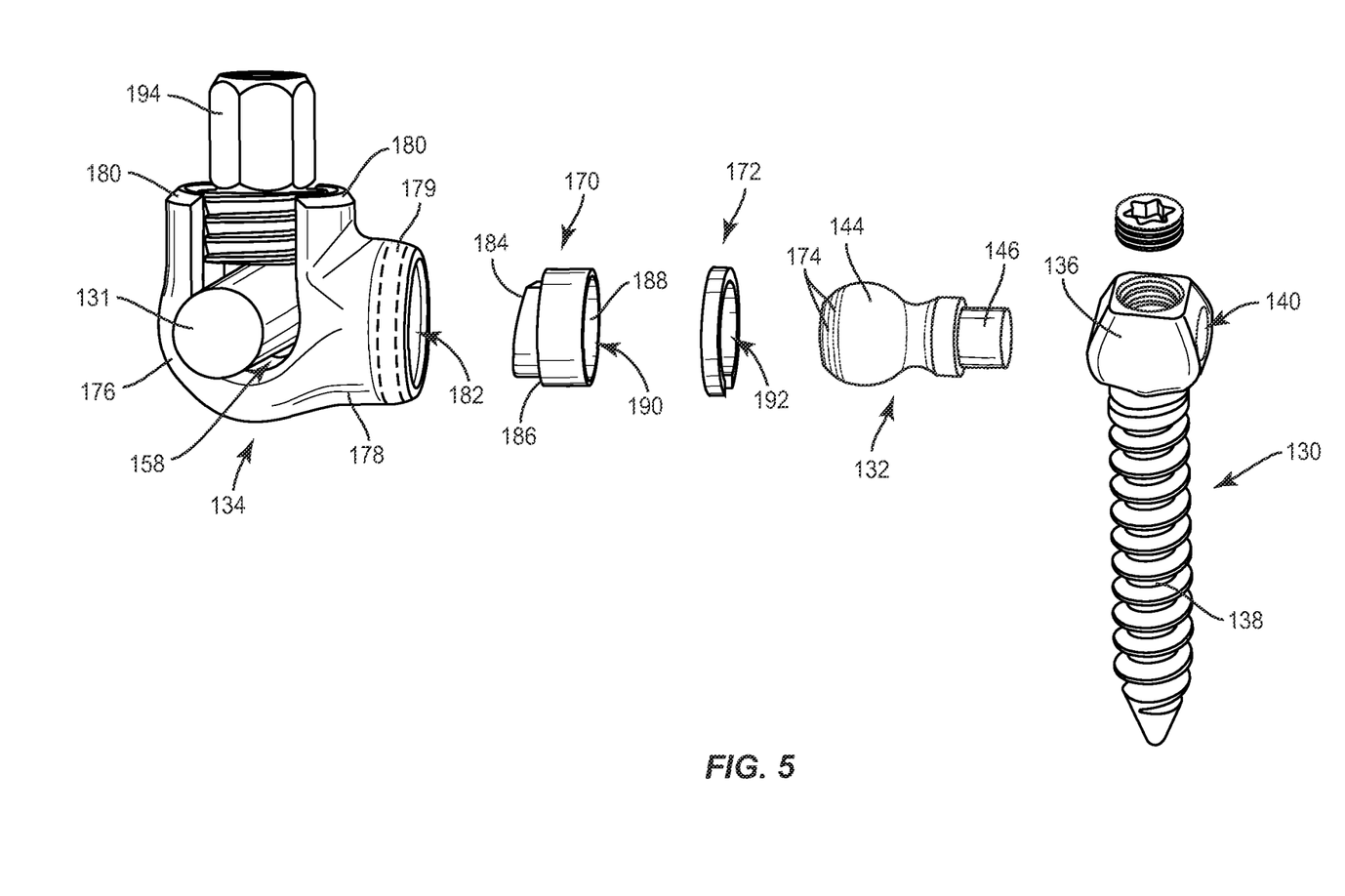
FIG. 5 is a perspective view of the components shown in FIG. 4 with parts separated.

In one embodiment, as shown in FIGS. 4 and 5, the implant system includes a bone screw 130, a connector 132, a receiver 134, a crown member 170 and a retaining member 172, similar to the components and methods of use described above. Bone screw 130 includes a proximal head 136 and a distal threaded shaft 138 configured to penetrate bone. Head 136 includes an inner surface that defines a first cavity 140 that defines an axis $A_4$. First cavity 140 is configured to receive and movably support at least a portion of connector 132 such that connector 132 can translate axially along axis $A_4$ within first cavity 140 through a plane, such as, for example, a coronal plane of the body. First cavity 140 has a tubular configuration for receiving a corresponding round portion of connector 132 and extends through head 136 of bone screw 130 so as to form a passageway through bone screw 130 along axis $A_4$. First cavity 140 is smooth and continuous such that first cavity 140 is free of any gaps or protrusions.

Connector 132 extends between a first end 144 and a second end 146. First end 144 forms part of a sphere or ball and includes a series of ridges 174 for improving purchase with the inside of crown member 170, as will be discussed. First end 144 may have alternative friction-increasing surface configurations such as roughening or knurling. First end 144 is shaped and sized to fit within an opening in crown member 170.

Second end 146 has a cylindrical outer surface, which is smooth, and continuous such that second end 146 is free of gaps or protrusions. Second end 146 has a diameter, which is less than that of first cavity 140 of bone screw 130 such that second end 146 may be received within first cavity 140 to retain connector 132 with bone screw 130. Second end 146 of connector 132 is configured for movement along axis $A_4$ within first cavity 140 of bone screw 130 for selective fixation in a position along first cavity 140. It is envisioned that second end 146 may be inserted into first cavity 140 and moved within first cavity 140 along axis $A_4$ in a first axial direction or a second axial direction oriented in an opposing direction to the first axial direction, by sliding second end 146 relative to first cavity 140. First cavity 140 is engageable with second end 146 to align the component parts in relative rotatable alignment.

Receiver 134 is attachable to first end 144 of connector 132 and includes a body portion 176 and an extension portion 178. An implant cavity 158 extends through body portion 176 and defines an axis $A_5$. Implant cavity 158 is configured to receive and movably support at least a portion of an implant, such as, for example, a vertebral rod 131, such that rod 131 can translate axially within implant cavity 158 along axis $A_5$. Implant cavity 158 is defined by a pair of upright branches 180, which define a U-shaped channel. Branches 180 may include internal threads to fix a coupling member, such as, for example, a setscrew 194 with receiver 134 to retain an implant within implant cavity 158. Implant cavity 158 is pivotable about an axis $A_6$ disposed transverse to axis $A_5$ such that an implant disposed in implant cavity 158 and lateral to first end 144 of connector 132 is pivotable in a first plane, such as, for example, a coronal plane of the body, relative to first end 144 of connector 132 in a configuration for selective fixation with first end 144 of connector 132. It is contemplated that at least a portion of rod 131 may be disposed within implant cavity 158 for relative movement in orientations relative to fifth axis $A_5$, such as, for example, transverse, perpendicular and/or other angular orientations such as acute or obtuse, co-axial and/or may be offset or staggered. It is further contemplated that at least a portion of rod 131 may be disposed within implant cavity 158 in alternate planes relative to a body, such as, for example, transverse and/or sagittal planes of a body. In one embodiment, implant cavity 158 may be disposed at an angle of about 30 to about 150 degrees relative to first cavity 140 of bone screw 130 and fifth axis $A_5$ may be disposed at an angle of about 30 to about 150 degrees relative to axis $A_4$.

Extension portion 178 of receiver 134 includes a transverse opening 182 extending through receiver 134 along axis $A_4$ configured to receive at least a portion of crown member 170 and first end 144 to pivotably connect receiver 134 with connector 132. Opening 182 defines a socket configured for moveable disposal of first end 144 of connector 132 such that receiver 134 is moveable relative to second end 146 of connector 132 in a plurality of axial orientations relative to axis $A_4$. Opening 182 has a diameter which is greater than that of first end 144 of connector 132 and/or crown member 170 such that at least a portion of first end 144 may be received within opening 182. Proximate to opening 182, extension portion 178 defines a groove 179 and associated ledge 181 (not shown) around opening 182. Groove 179 extends around the perimeter of opening 182. It is envisioned that groove 179 could extend only partially around the perimeter of opening 182. Groove 179 has a groove depth and a groove diameter.

Crown member 170 is in the shape of a circular disc, having a posterior surface 184 with a beveled edge 186 and an anterior surface 188. Anterior surface 188 is configured to accommodate first end 144 of connector 132 and has the shape of part of a sphere. It is envisioned that anterior surface 188 of crown member 170 can have one or more other shapes, such as beveled or conical anterior surface 188. Anterior surface 188 can be provided with a friction or purchase enhancing surface configuration (e.g. roughening or knurling) for cooperation with first end 144 of connector 132. Crown member 170 also includes an aperture 190 configured so that first end 144 of connector 132 may be accessed through crown member 170. Crown member 170 and first end 144 of connector 132 form an articulating joint to attach receiver 134 to first end 144 of connector 132 such that receiver 134 is moveable relative to second end 146 of connector 132 in a plurality of axial orientations relative to axis $A_4$. Crown member 170 is sized and shaped to fit within opening 182 of receiver 134. The outer dimension of crown member 170 is slightly smaller than the inner dimension of opening 182 so that crown member 170 is slidably and rotatably movable within opening 182.

Retaining member 172 has the form of a C-shaped spring or clip defining an aperture 192. In one embodiment, retaining member 172 includes an internal surface, which forms a portion of a sphere of radius substantially identical to the radius of first end 144 of connector 132. The diameter of aperture 192 is smaller than the diameter of first end 144 of connector 132 and the diameter of crown member 170. Retaining member 172 has an unloaded or natural outer diameter measured when retaining member 172, which is less than the groove diameter of groove 179. Further, retaining member 172 has a body width that is substantially constant throughout retaining member 172 and is greater than the groove depth of groove 179.

Connector 132, crown member 170 and retaining member 172 are inserted into receiver 134 through opening 182 in extension portion 178 of receiver 134, either individually or substantially in one step. For example, crown member 170 may be inserted first, followed by connector 132 with retaining member 172 being inserted last.

Retaining member 172 may be fitted around first end 144 of connector 132 prior to insertion of first end 144 of connector 132 into receiver 134. Ridges 174 on first end 144 of connector 132 are pressed into anterior surface 188 of crown member 170 such that connector 132 is locked into the desired angular position with respect to an implant inserted into implant cavity 158 of receiver 134. Retaining member 172 can be placed around first end 144 of connector 132 by inserting first end 144 of connector 132 through aperture 182 of retaining member 172 and moving retaining member 172 over first end 144 of connector 132. By placing crown member 170 with first end 144 of connector 132 so that anterior surface 188 of crown member 170 adjoins first end 144 of connector 132, and fitting first end 144 of connector 132 and retaining member 172 together as described above, simultaneous insertion of connector 132, crown member 170 and retaining member 172 into receiver 134 can be accomplished.

Crown member 170 remains slideably and rotatably positioned in opening 182 of receiver 134, and first end 144 of connector 132 remains multi-axially moveable with respect to crown member 170 and receiver 134. Retaining member 172 is forced into opening 182 of receiver 134. Retaining member 172 contracts, making the gap in retaining member 172 smaller until the outer diameter of retaining member 172 is the same as the diameter of first end 144 of connector 132. Retaining member 172 is further advanced along opening 182 and into groove 179 so that retaining member 172 is fitted into at least a portion of groove 179. The groove diameter of groove 179 is smaller than the outer diameter of retaining member 172 in its natural (i.e., unloaded) condition such that when retaining member 172 is within groove 179, retaining member 172 presses against the walls of groove 179. It is envisioned that the groove diameter of groove 179 may be the same size or slightly larger than the natural outer diameter of retaining member 172 in which case a surface of retaining member 172 rests upon a ledge of groove 179 to hold retaining member 172 within groove 179. The groove depth of groove 179 is less than the body width of retaining member 172 such that a portion of retaining member 172 projects into opening 182 when retaining member 172 is fitted within groove 179. Connector 132 and crown member 170 are retained within opening 182 of receiver 134 when retaining ring 172 is seated within groove 179. Crown member 170 is supported by first end 144 of connector 132, and connector 132 is supported by an internal of retaining member 172. Retaining member 172 is held by groove 179 and thus connector 132 and crown member 170 will not pass through retaining ring 172 and out of receiver 134 when retaining ring 172 is within groove 179.

Figure 6:
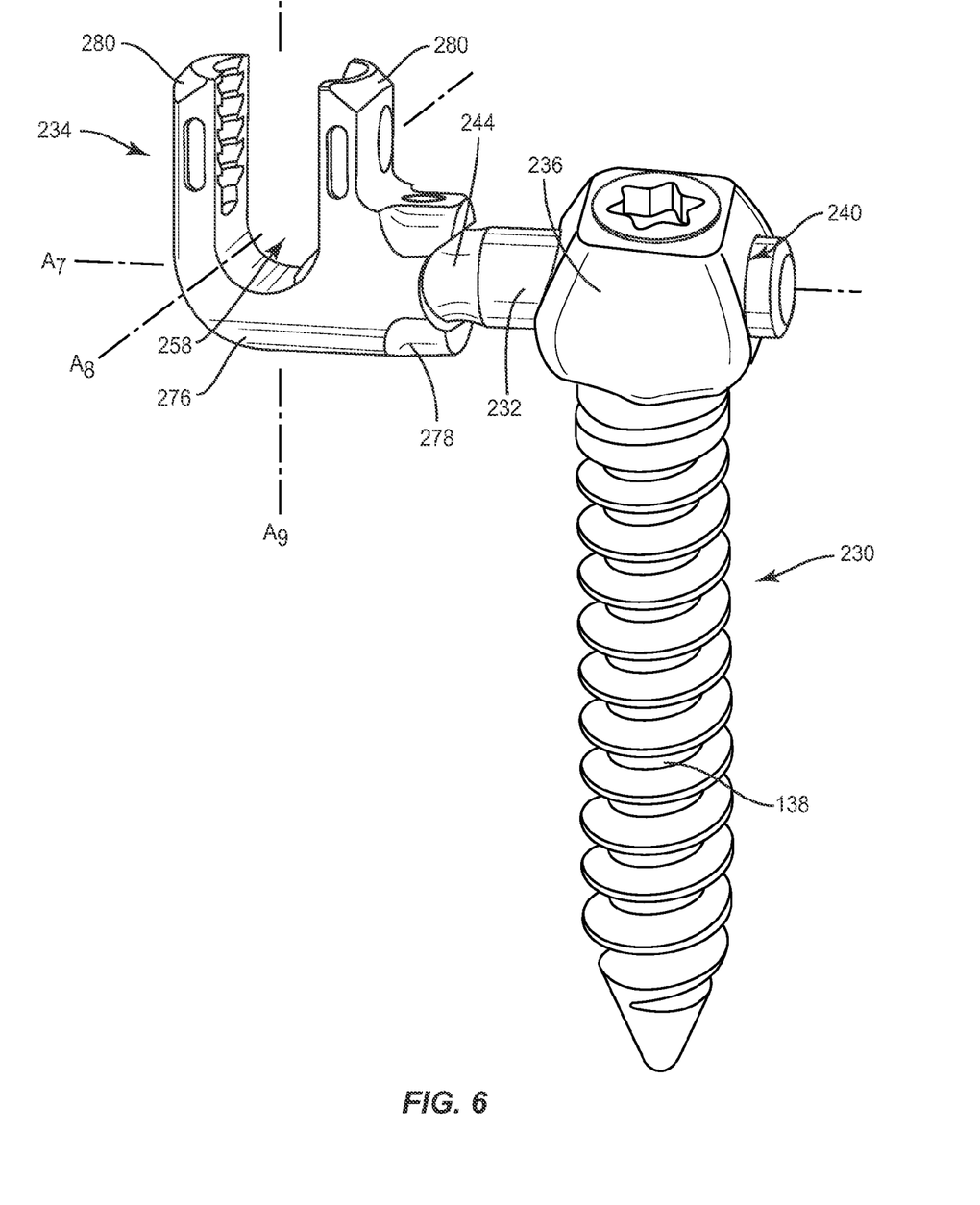
FIG. 6 is a perspective view of one embodiment of components of the implant system shown in FIG. 1.
Figure 7:
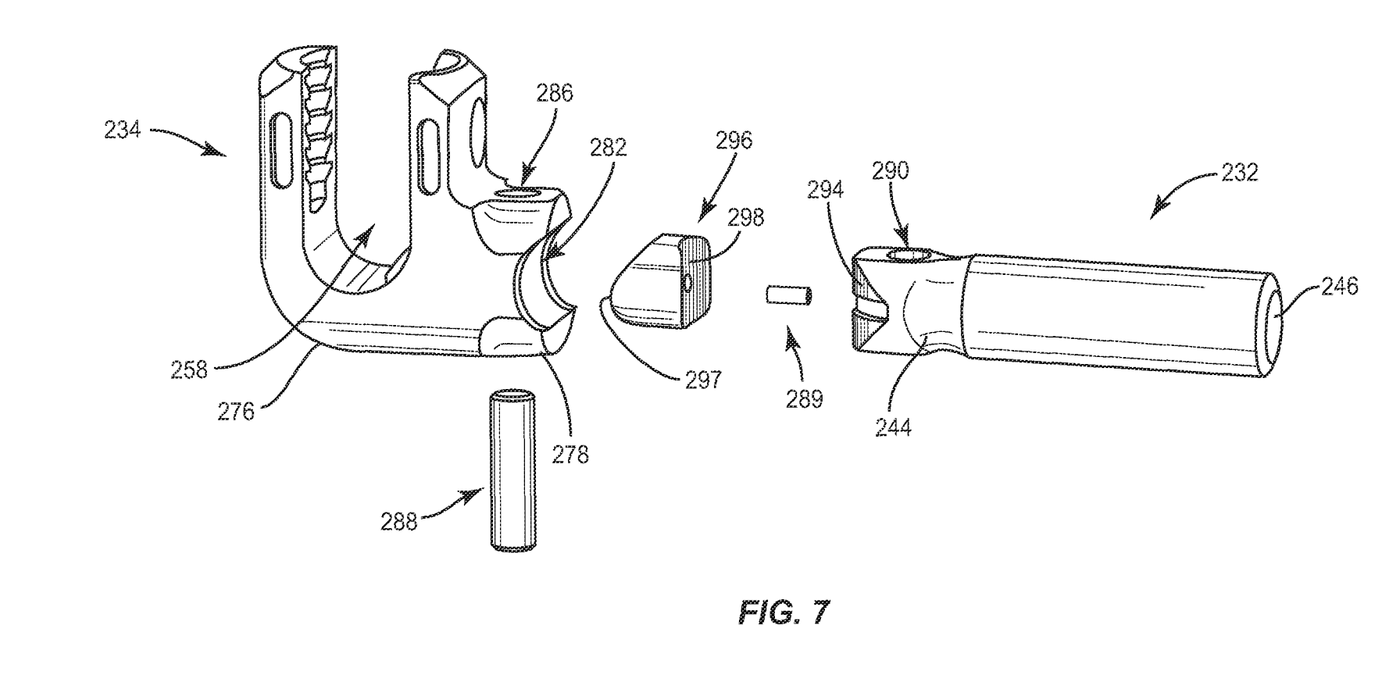
FIG. 7 is a perspective view of a connector of the implant system shown in FIG. 6 with parts separated.

In one embodiment, as shown in FIGS. 6 and 7, the implant system includes a bone screw 230, a connector 232 and a receiver 334, similar to the components and methods of use described above. Bone screw 230 includes a proximal head 236 and a distal threaded shaft 238 configured to penetrate bone. Head 236 includes an inner surface that defines a first cavity 240 that defines an axis $A_7$. First cavity 240 is configured to receive and movably support at least a portion of connector 232 such that connector 232 can translate axially along axis $A_7$ within first cavity 240 through a plane, such as, for example, a coronal plane of the body. First cavity 240 has a tubular configuration for receiving a corresponding round portion of connector 232 and extends through head 236 of bone screw 230 so as to form a passageway through bone screw 230 along axis $A_7$. First cavity 240 is smooth and continuous such that first cavity 240 is free of any gaps or protrusions.

Connector 232 is a substantially cylindrical shaft that extends between a first end 244 and a second end 246. First end 244 includes a first face, such as, for example, an end face 294 including a first splined surface configured to mate with splines on a surface of receiver 234 to releasably fix receiver 234 with connector 232 in a selected rotatable position in a plane, such as, for example, a coronal plane of the body relative to shaft 238 of bone screw 230. End face 294 includes a transverse bore 295 (not shown) extending into end face 294 configured to receive at least a portion of a pin to separate the first splined surface of connector 232 from the second splined surface of receiver 234. Connector 232 includes an aperture 292 extending through first end 244 of connector 232 configured to receive a pin to lock connector 232 in position relative to receiver 234.

Second end 246 has a cylindrical outer surface, which is smooth, and continuous such that second end 246 is free of gaps or protrusions. Second end 246 has a diameter which is less than that of first cavity 240 of bone screw 230 such that second end 246 may be received within first cavity 240 retain connector 232 with bone screw 230. Second end 246 of connector 232 is configured for movement along axis $A_7$ within first cavity 240 of bone screw 230 for selective fixation in a position along first cavity 240. It is envisioned that second end 246 may be inserted into first cavity 240 and moved within first cavity 240 along axis $A_7$ in a first axial direction or a second axial direction oriented in an opposing direction to the first axial direction, by sliding second end 246 relative to first cavity 240. First cavity 240 is engageable with second end 246 to align the component parts in relative rotatable alignment.

Receiver 234 is attachable to first end 244 of connector 232 and includes a body portion 276 and an extension portion 278. An implant cavity 258 extends through body portion 276 and defines an axis $A_8$. Implant cavity 258 is configured to receive and movably support at least a portion of an implant, such as, for example, a vertebral rod, such that the rod can translate axially within implant cavity 258 along axis $A_8$. Implant cavity 258 is defined by a pair of upright branches 280, which define a U-shaped channel. Branches 280 may include internal threads to fix a coupling member, such as, for example, a setscrew with receiver 234 to retain an implant within implant cavity 258. Implant cavity 258 is pivotable about an axis $A_9$ disposed transverse to axis $A_8$ such that an implant disposed in implant cavity 258 and lateral to first end 244 of connector 232 is pivotable in a plane, such as, for example, a coronal plane of the body, relative to first end 244 of connector 232 in a configuration for selective fixation with first end 244 of connector 232. It is contemplated that at least a portion of an implant may be disposed within implant cavity 258 for relative movement in orientations relative to axis As, such as, for example, transverse, perpendicular and/or other angular orientations such as acute or obtuse, co-axial and/or may be offset or staggered. It is further contemplated that at least a portion of an implant may be disposed within implant cavity 258 in alternate planes relative to a body, such as, for example, transverse and/or sagittal planes of a body. In one embodiment, implant cavity 258 may be disposed at an angle of about 30 to about 150 degrees relative to first cavity 240 of bone screw 230 and axis $A_8$ may be disposed at an angle of about 30 to about 150 degrees relative to axis $A_7$.

Extension portion 278 of receiver 234 includes a transverse opening 282 extending along axis $A_7$ configured to receive at least a portion of an insert 296 and/or first end 244 to pivotably connect receiver 234 with connector 232. Opening 282 has a diameter that is greater than first end 244 of connector 132 and/or insert 296 such that at least a portion of first end 244 and/or insert 296 may be received within opening 282. Extension portion 278 further includes a longitudinal opening 286 positioned perpendicular to transverse opening 282 configured to receive a pin to lock connector 232 in position relative to receiver 234.

Insert 296 of receiver 234 extends between an arcuate posterior wall 297 and an end face 298 defining a second spline surface that is engageable with the first spline surface on end face 294 of connector 232 to fix receiver 234 with connector 232 and align receiver 234 with axis $A_7$. End face 298 includes a transverse bore 299 (not shown) extending into end face 298 configured to receive at least a portion of a pin to separate the first splined surface of connector 232 from the second splined surface of receiver 234. Posterior wall 297 is continuous with implant cavity 258 when insert 296 is positioned within opening 282 in receiver 234 such that there are no gaps or protrusions between insert 296 and implant cavity 258. It is envisioned that insert 296 may be prevented from being inserted into implant cavity 258 by a boss or stop within opening 282 in extension portion 278 of receiver 234.

Second end 246 of connector 232 is inserted into first cavity 240 of bone screw 230 to connect bone screw 230 with connector. End face 294 of connector 232 then engages end face 298 of insert 296 when insert 296 is positioned within opening 282 in extension portion 278 of receiver 234 such that the first and second splined surfaces engage one another to fix receiver 234 with connector 232 and align receiver 234 with axis $A_7$ in angular increments corresponding to a spline teeth angle of the splines which define the first and second splined surfaces. In one embodiment, the spline teeth angle is 15 degrees. It is contemplated that the spline teeth angle may be in the range of approximately 5 to 20 degrees. Receive 234 (including implant cavity 258) is pivotable about axis $A_9$ such that an implant disposed in implant cavity 258 and lateral to first end 244 of connector 232 is selectively pivotable in a coronal plane of the body relative to first end 244 of connector 232 in a configuration for selective angular fixation with first end 244 of connector 232. A silicone pin 298 may be inserted into bore 295 in end face 294 and bore 299 in end face 298 to separate the first and second spline surfaces to prevent the same from engaging one another. Once receiver 234 is positioned in the desired orientation relative to connector 232, a pin 288 may be inserted through opening 286 in extension portion 278 of receiver 234 and opening 290 in first end 244 of bone screw 230 to prevent receiver 234 from pivoting relative to connector 232.

In one embodiment, the implant system includes an agent, which may be disposed, packed or layered within, on or about the components and/or surfaces of the implant system. It is envisioned that the agent may include bone growth promoting material, such as, for example, bone graft to enhance fixation of the fixation elements with vertebrae V.

It is contemplated that the agent may include therapeutic polynucleotides or polypeptides. It is further contemplated that the agent may include biocompatible materials, such as, for example, biocompatible metals and/or rigid polymers, such as, titanium elements, metal powders of titanium or titanium compositions, sterile bone materials, such as allograft or xenograft materials, synthetic bone materials such as coral and calcium compositions, such as HA, calcium phosphate and calcium sulfite, biologically active agents, for example, gradual release compositions such as by blending in a bioresorbable polymer that releases the biologically active agent or agents in an appropriate time dependent fashion as the polymer degrades within the patient. Suitable biologically active agents include, for example, BMP, Growth and Differentiation Factors proteins (GDF) and cytokines. The components of the implant system can be made of radiolucent materials such as polymers. Radiomarkers may be included for identification under x-ray, fluoroscopy, CT or other imaging techniques. It is envisioned that the agent may include one or a plurality of therapeutic agents and/or pharmacological agents for release, including sustained release, to treat, for example, pain, inflammation and degeneration.

It is envisioned that the use of microsurgical and image guided technologies may be employed to access, view and repair spinal deterioration or damage, with the aid of the implant system. Upon completion of a procedure employing the implant system described above, the surgical instruments and assemblies are removed and the incision is closed.

It will be understood that various modifications may be made to the embodiments disclosed herein. Therefore, the above description should not be construed as limiting, but merely as exemplification of the various embodiments. Those skilled in the art will envision other modifications within the scope and spirit of the claims appended hereto.

What is claimed is:

1. An implant system comprising:
    a fastener including a proximal portion and a distal portion, the proximal portion including an inner surface that defines a first cavity that defines a first axis, the distal portion being configured for penetrating tissue and defining a longitudinal axis disposed transverse to the first axis;
    a connector extending between a first end and a second end configured for disposal in the first cavity, the first end of the connector including a side surface defined between a lower surface and an upper surface of the first end of the connector; and
    a receiver attachable to the first end of the connector and including a laterally extending arcuate arm, the side surface and the arcuate arm defining an implant cavity defining a second axis, the implant cavity being configured for disposal of an implant such that the implant engages an inner surface of the arcuate arm and the side surface, the implant cavity being rotatable about a third axis disposed transverse to the second axis such that an implant disposed in the implant cavity and lateral to the first end of the connector is rotatable in a first plane relative to the first end of the connector in a configuration for selective fixation with the first end of the connector,
    wherein the first end of the connector includes a first disk being disposed in a co-axial orientation with the second end of the connector and the implant, the first disk having a first splined surface, and the receiver including a second disk having a second splined surface that mates with the first splined surface.

2. The implant system of claim 1, wherein the first disk includes a shaft extending in a posterior orientation, and the receiver includes an opening configured for disposal of the shaft.

3. The implant system of claim 2, wherein the shaft is threaded and the receiver includes a nut engageable with the threaded shaft to retain the receiver with the connector.

4. The implant system of claim 3, wherein the nut is a separate component from the receiver.

5. The implant system of claim 1, wherein the first plane is a coronal plane of a body.

6. The implant system of claim 1, wherein the implant is rotatable to a selected angular orientation for fixation with the first end of the connector.

7. The implant system of claim 1, wherein the inner surface of the proximal portion includes axial splines oriented along the first axis and circumferentially disposed about the inner surface.

8. The implant system of claim 1, wherein the second end of the connector includes an outer surface including axial splines circumferentially disposed about the outer surface of the second end of the connector.

9. The implant system of claim 1, wherein the inner surface of the proximal portion includes axial splines oriented along the first axis and circumferentially disposed thereabout and the second end of the connector includes axial splines circumferentially disposed thereabout, the axial splines of the proximal portion being engageable with the axial splines of the connector in a configuration for selective angular fixation of the fastener with the connector.

10. The implant system of claim 1, wherein the first end of the connector defines an end face including a first spline surface and the receiver includes an end face including a second spline surface, the spline surfaces being engageable to fix the receiver with the connector and align the receiver with the first axis.

11. The implant system of claim 1, wherein the first end of the connector includes a shaft that defines an end face including a first spline surface and the receiver includes an insert that defines an end face including a second spline surface, the spline surfaces being engageable to fix the receiver with the connector and align the receiver with the first axis.

12. The implant system of claim 1, wherein the receiver defines a posterior opening configured to receive the implant.

13. The implant system of claim 1, wherein the receiver defines an anterior opening configured to receive the implant.

14. A method for treating a disorder, the method comprising the steps of:
    providing the implant system recited in claim 1;
    attaching the distal portion of the fastener with iliac bone;
    disposing the implant in the implant cavity such that the implant is lateral to the first end of the connector and the implant engages an inner surface of the arcuate arm and the side surface;
    selectively rotating the implant in the first plane; and
    locking the receiver with the connector in a selected angular orientation of the implant relative to the connector.

15. The implant system of claim 1, wherein the side surface is tapered.

16. The implant system of claim 1, wherein the receiver includes an upper surface and a bottom splined surface, the arcuate arm including a distal tip being curved below the bottom splined surface of the receiver.

17. The implant system of claim 1, wherein the arcuate arm extends laterally from an arcuate side surface of receiver.

18. The implant system of claim 1, wherein the implant is rotatable about an axis that extends parallel to the longitudinal axis such that the implant extends transverse to the first axis.

19. The implant system of claim 1, further comprising the implant, wherein the implant is a spinal rod having a cylindrical cross sectional configuration.

20. An implant system comprising:
   an iliac bone screw including a posterior head and an anterior threaded shaft configured to penetrate bone, the posterior head including an inner surface that defines a first cavity that defines a first axis, the inner surface including axial splines oriented along the first axis and circumferentially disposed about the inner surface, the distal portion defining a longitudinal axis disposed transverse to the first axis;
   a connector extending between a first end and a second end, the first end including a first disk having a first face including a threaded shaft extending in a posterior orientation therefrom and defining a first splined surface, the first end of the connector further including a side surface defined between the first face and a second face, the second end including an outer surface comprising axial splines circumferentially disposed thereabout, the axial splines of the posterior head being engageable with the axial splines of the second end in a configuration for selective angular fixation of the iliac bone screw with the connector; and
   a receiver including a second disk having a second splined surface that mates with the first splined surface and defining an opening configured for disposal of the shaft, the receiver further including a nut engageable with the threaded shaft to retain the receiver with the connector, the receiver further including a laterally extending arcuate arm, the side surface and the arcuate arm defining an implant cavity defining a second axis, the implant cavity being configured for disposal of vertebral rod such that the vertebral rod engages an inner surface of the arcuate arm and the side surface,
   wherein the implant cavity is rotatable about a third axis disposed transverse to the second axis such that a vertebral rod disposed in the implant cavity and lateral to the first end of the connector is selectively rotatable in a coronal plane of a body relative to the first end of the connector in a configuration for selective angular fixation with the first end of the connector.

* * * * *